(12) United States Patent
Robinson et al.

(10) Patent No.: US 6,884,122 B2
(45) Date of Patent: Apr. 26, 2005

(54) LEAD FRAME AND STRIP MOLDING FOR CONTACT CONNECTORS IN IMPLANTABLE MEDICAL DEVICES

(75) Inventors: Scott J. Robinson, Forest Lake, MN (US); John E. Kast, Hugo, MN (US); Andrew J. Ries, Lino Lakes, MN (US); Mary A. Fraley, Minnetonka, MN (US); Jeffrey J. Clayton, Ramsey, MN (US); Randy Roles, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/045,340

(22) Filed: Oct. 25, 2001

(65) Prior Publication Data

US 2003/0082958 A1 May 1, 2003

(51) Int. Cl.⁷ .................................................. H01R 9/22
(52) U.S. Cl. ........................ 439/722; 439/885; 439/909; 607/128
(58) Field of Search .................................. 439/885, 722, 439/909, 910, 887, 606; 29/858, 883, 860; 607/37, 128

(56) References Cited

U.S. PATENT DOCUMENTS

| | | | | |
|---|---|---|---|---|
| 3,585,570 | A | * | 6/1971 | Jans ........................... 439/439 |
| 4,375,817 | A | | 3/1983 | Engle et al. ............. 128/419 D |
| 4,870,227 | A | * | 9/1989 | Saen et al. ................... 439/887 |
| 4,894,021 | A | * | 1/1990 | Holden et al. .............. 439/191 |
| 5,057,650 | A | * | 10/1991 | Urushibata et al. ......... 439/465 |
| 5,782,892 | A | * | 7/1998 | Castle et al. ................ 439/909 |
| 6,029,089 | A | * | 2/2000 | Hawkins et al. ............ 439/909 |
| 6,059,601 | A | * | 5/2000 | Hirai et al. ................... 29/883 |
| 6,351,884 | B1 | * | 3/2002 | Damaschke et al. .......... 29/865 |

* cited by examiner

*Primary Examiner*—P. Austin Bradley
*Assistant Examiner*—Felix O. Figueroa
(74) *Attorney, Agent, or Firm*—Girma Wolde-Michael; Paul H. McDowall

(57) ABSTRACT

An apparatus and method of electrically connecting components of an implantable medical device are disclosed. One embodiment is an apparatus having at least one electrical connector comprising a tab section and a housing at least partially enclosing the electrical connectors, wherein the housing is molded into sealing engagement with the electrical connectors and the tab section is capable of removal from the electrical connector after the housing is molded.

37 Claims, 16 Drawing Sheets

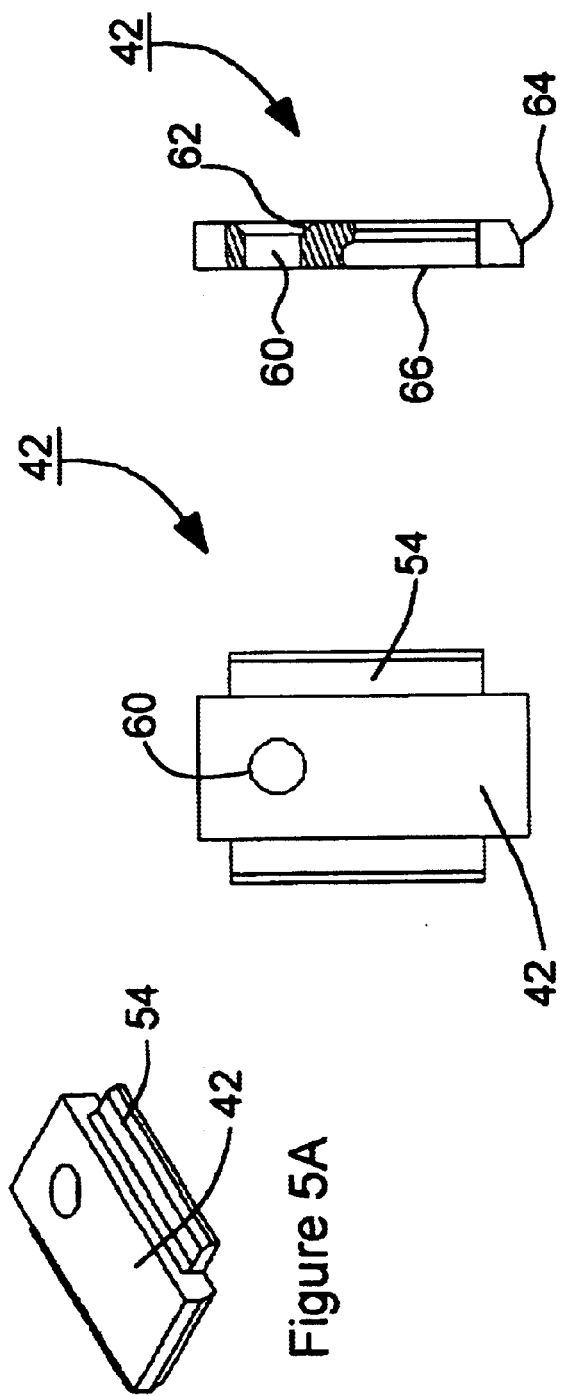

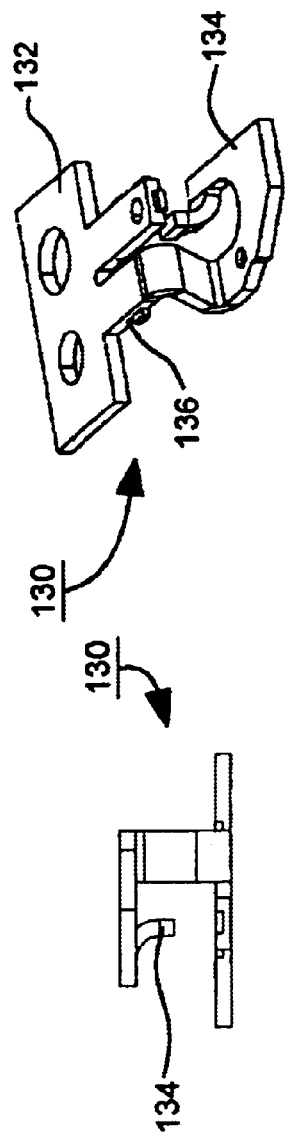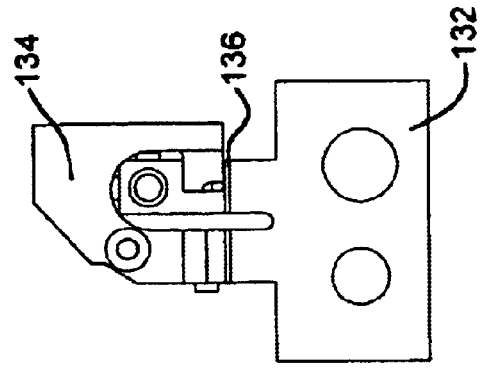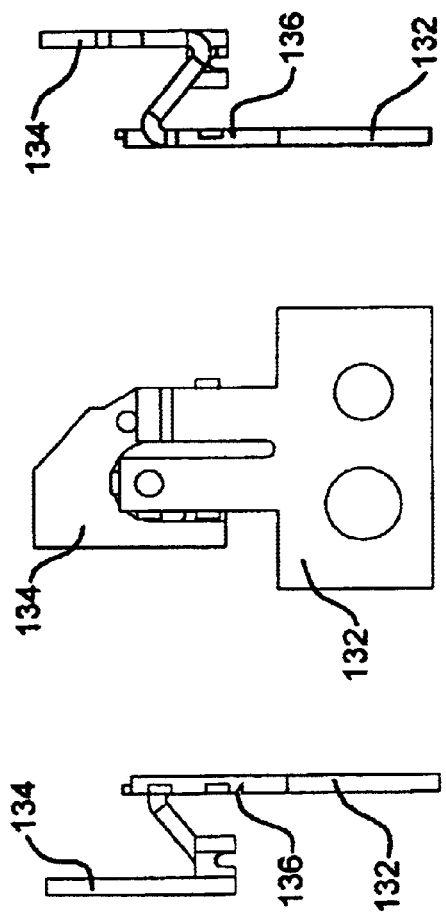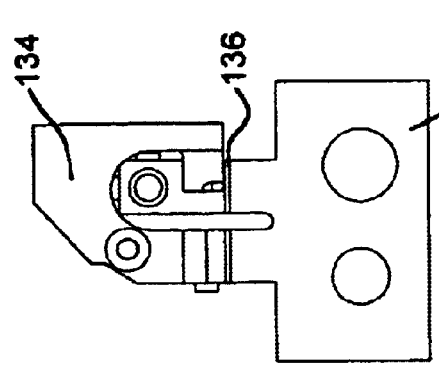

LEAD FRAME AND STRIP MOLDING FOR CONTACT CONNECTORS IN IMPLANTABLE MEDICAL DEVICES

BACKGROUND OF THE INVENTION

1. Field of the Invention

This invention relates generally to medical devices, and, more particularly, to contact connectors used in implantable medical devices.

2. Description of the Related Art

Since their earliest inception some forty years ago, there has been a significant advancement in body-implantable electronic medical devices. Today, these implantable devices include therapeutic and diagnostic devices, such as pacemakers, cardioverters, defibrillators, neural stimulators, drug administering devices, among others for alleviating the adverse effects of various health ailments. Today's implantable medical devices are also vastly more sophisticated and complex than their predecessors, and are therefore capable of performing considerably more complex tasks for reducing the effects of these health ailments.

A variety of different implantable medical devices (IMD) are available for therapeutic stimulation of the heart and are well known in the art. For example, implantable cardioverter-defibrillators (ICDs) are used to treat patients suffering from ventricular fibrillation, a chaotic heart rhythm that can quickly result in death if not corrected. In operation, the ICD continuously monitors the electrical activity of a patient's heart, detects ventricular fibrillation, and in response to that detection, delivers appropriate shocks to restore normal heart rhythm. Similarly, an automatic implantable defibrillator (AID) is available for therapeutic stimulation of the heart. In operation, an AID device detects ventricular fibrillation and delivers a nonsynchronous high-voltage pulse to the heart through widely spaced electrodes located outside of the heart, thus mimicking transthoratic defibrillation. Yet another example of a prior art cardioverter includes the pacemaker/cardioverter/defibrillator (PCD) disclosed, for example, in U.S. Pat. No. 4,375,817 to Engle, et al. This device detects the onset of tachyarrhythmia and includes means to monitor or detect progression of the tachyarrhythmia so that progressively greater energy levels may be applied to the heart to interrupt a ventricular tachycardia or fibrillation. Numerous other, similar implantable medical devices, for example a programmable pacemaker, are further available.

Regardless of the exact construction and use, each of the above-described IMDs generally comprise certain primary components: a control circuit, an output circuit, a power source and a hermetic feedthrough. The control circuit monitors and determines various operating characteristics, such as, for example, rate, synchronization, pulse width and output voltage of heart stimulating pulses, as well as diagnostic functions such as monitoring the heart. An output circuit generates electrical stimulating pulses to be applied to the heart via one or more leads in response to signals from the control circuit.

The power source "powers" both the low-power control circuit and the high-power output circuit. As a point of reference, the power source is typically required to provide 10–20 microamps to the control circuit and a high power pulse to the output circuit. Depending upon the particular IMD application, the output circuit may require a stimulation energy of as little as 0.1 Joules for pacemakers to as much as 40 Joules for implantable defibrillators. In addition to providing sufficient stimulation energy, the power source must possess a low self-discharge to have a useful life of many years, must be highly reliable, and must be able to supply energy from a minimum packaged volume.

The various components of an implantable medical device require electrical connectors that can provide a secure electrical path. The connectors must provide a complete, non-corrosive, and preferably economical means of linking the various electrical components of the medical device. Any incomplete connection of the electrical components within the implantable medical device may cause the device to function improperly or otherwise cause it to cease operating altogether. In addition, because the medical device is surgically implanted within the patient's body, accessibility to the device is difficult for repair or replacement subsequent to implantation. If the implantable medical device functions improperly or fails altogether as a result of an incomplete connection, it may prove fatal to the patient.

Typical connectors in use today comprise a base metal that can have a plating of a second material applied that has certain desired properties such as corrosion resistance. The plating material can comprise specialty metals such as nickel or gold that is applied using an electrolytic plating process. Currently, individually manufactured contacts are used for the electrical connectors in implantable medical devices. These individual connections can collectively comprise a substantial expense and take considerable time to position and secure within the device or component housing. A typical medical device such as a pacemaker or a neural stimulator will have multiple electrical connections between components, each requiring its own physical connection. Thus, with an increase in the number of electrical connections that are made within a particular device, more time and expense may be spent making the required connections between components. Having a number of individual connectors placed, secured and connected between the various components of an implantable medical device may increase the device failure rate, since multiple steps are required within the process.

There is a need for improved electrical contact connector design and means of manufacture.

SUMMARY OF THE INVENTION

An apparatus and method of electrically connecting components of an implantable medical device are disclosed. One embodiment is an apparatus comprising at least one electrical connector and a housing at least partially enclosing the at least one electrical connector, wherein the housing is molded into sealing engagement with the electrical connectors.

An alternate embodiment of the invention is an electrical connector comprising an insert comprising a plurality of electrical contacts. A connecting tab connects the plurality of electrical contacts together. An insulating housing is molded in contact with the plurality of electrical contacts. The electrical connector is a component in an implantable medical device. The connecting tab is detachable from the plurality of electrical contacts, leaving discrete contacts after removal Yet another embodiment is a method for electrically connecting components of an implantable medical device. The method includes providing a molded electrical connector comprising a plurality of electrical contacts and inserting the electrical connector within an implantable medical device. Components of the implantable medical device are electrically connected to the electrical connector, thereby electrically connecting the components of the implantable medical device together.

BRIEF DESCRIPTION OF THE DRAWINGS

The invention may be understood by reference to the following description taken in conjunction with the accompanying drawings, in which like reference numerals identify like elements, and in which:

FIGS. 5A–D shows multiple views of an electrical contact after a connection tab is removed within an embodiment of the present invention;

FIGS. 15A–F show multiple perspective views in which the stamped insert 130 is bent and reconfigured into a three dimensional insert.

Figure 1:
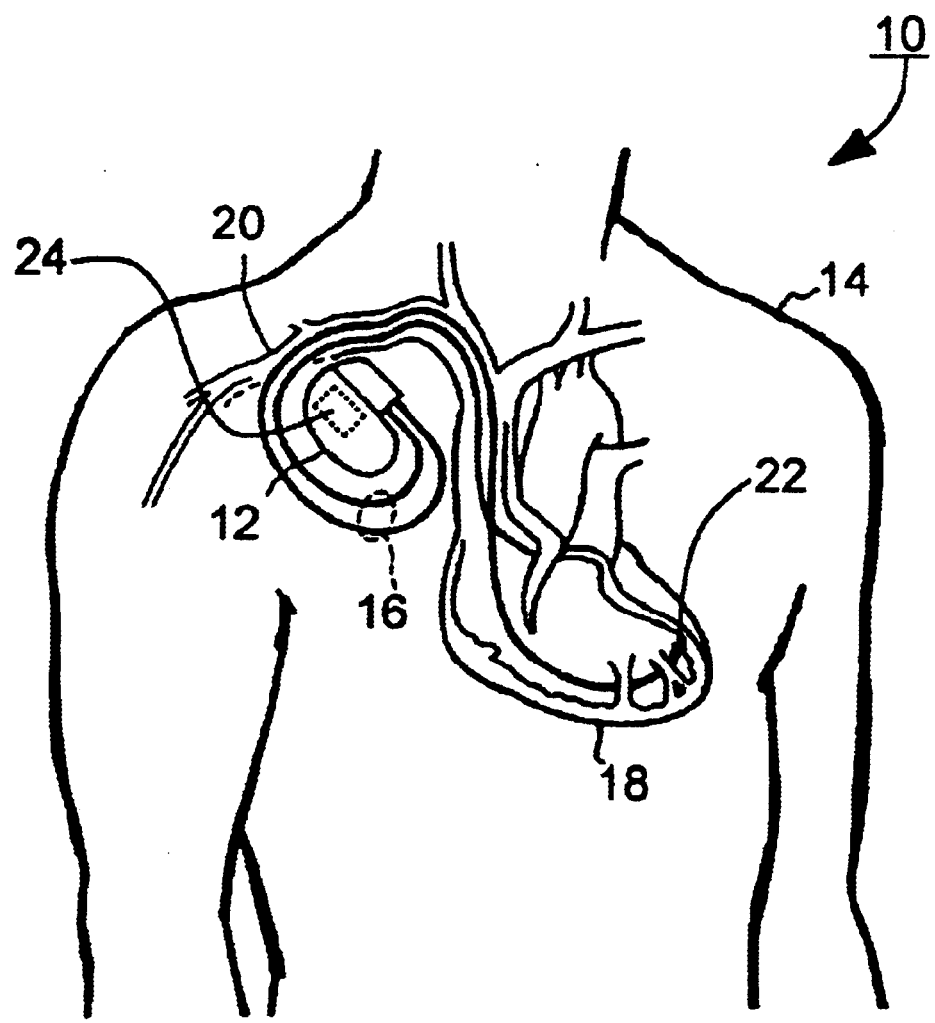
FIG. 1 schematically illustrates one embodiment of a prior art implanted medical device in the form of a pacemaker and associated leads positioned to stimulate and/or sense the heart.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning now to the drawings, and specifically referring to FIG. 1, one embodiment of a prior art implantable medical device (IMD) system 10 is shown. The IMD system 10 includes an implantable electronic device 12 that has been implanted in a patient 14. The device 12 may take the form of a pacemaker, cardioverter, defibrillator, neural stimulator or drug administering device. It will be appreciated, however, that this list of examples is not exhaustive, and may take the form of a variety of other devices.

The device 12 is housed within a hermetically sealed, biologically inert outer housing or container, which may itself be conductive so as to serve as an electrode in the pacemaker's pacing/sensing circuit. One or more pacemaker leads, which are collectively identified by reference numeral 16, are electrically coupled to the device 12 and extend into the patient's heart 18 through a cardiac vessel 20, such as a vein. Disposed generally near a distal end of the leads 16 are one or more exposed conductive electrodes 22 for sensing cardiac activity, delivering electrical pacing stimuli (i.e., therapeutic signals) to the heart 18, or providing a stimulating voltage to defibrillate the heart 18. The leads 16 may be implanted with their distal end situated adjacent the atrium or the ventricle, or both, of the heart 18. A battery 24, which is an integral part of the implantable device 12, provides power thereto.

Figure 2:
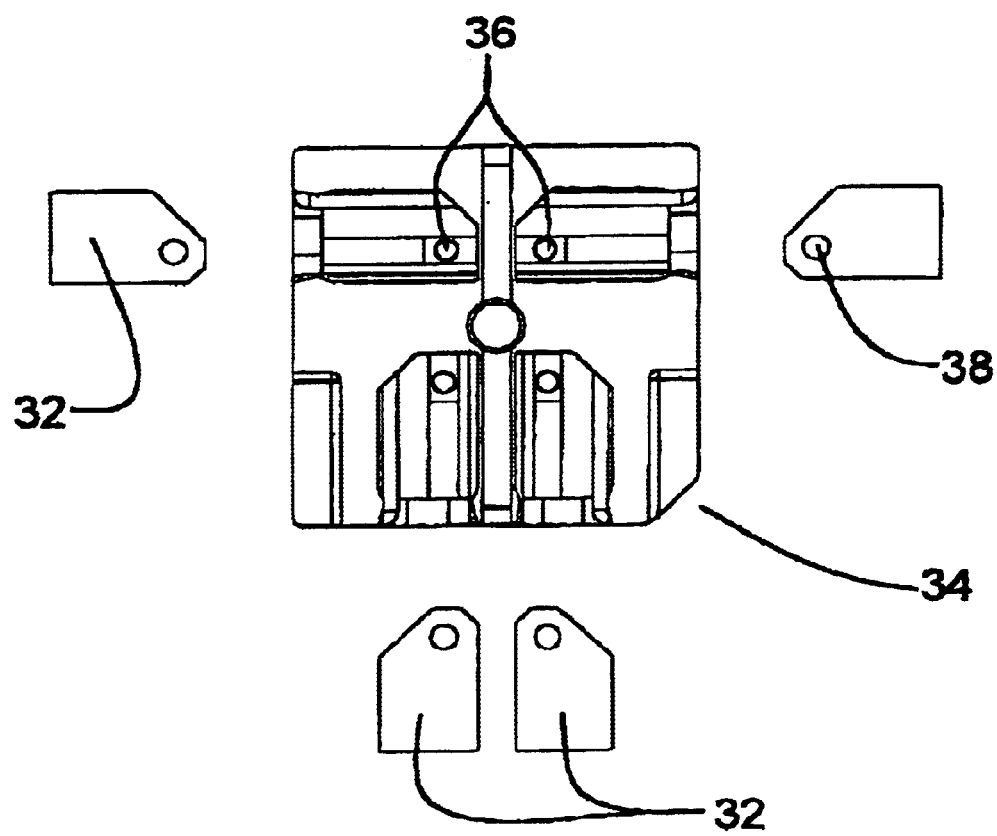
FIG. 2 depicts a prior art connector in an unassembled and assembled state, respectively, said prior art connector having individually manufactured contacts placed in a plastic housing.

FIG. 2 shows a photograph of a typical prior art connector 30 that is individually manufactured. Multiple individual contacts 32 are placed inside a plastic housing 34. Holes 36 within the housing are aligned with holes 38 in the contacts 32 and provide a pathway for electrical wires (not shown) to pass through the holes 36, 38 and be connected to the contacts 32.

Figure 3A:
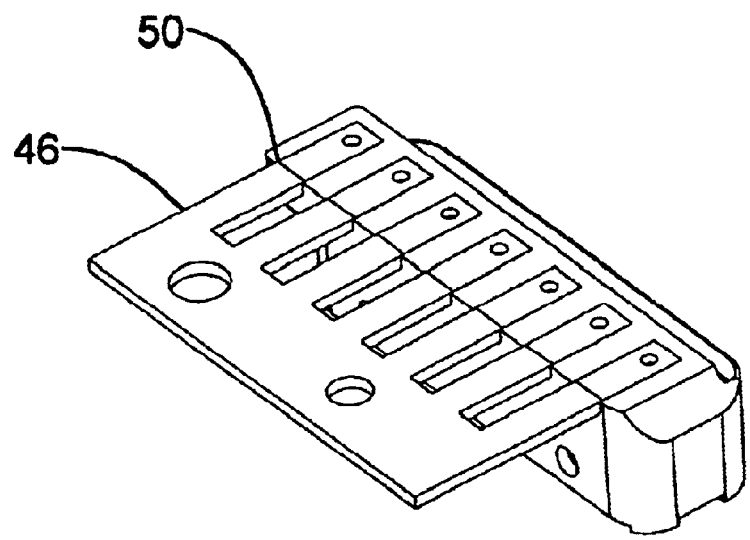
FIG. 3 shows an embodiment of the invention comprising multiple contact strip molding.
Figure 3B:
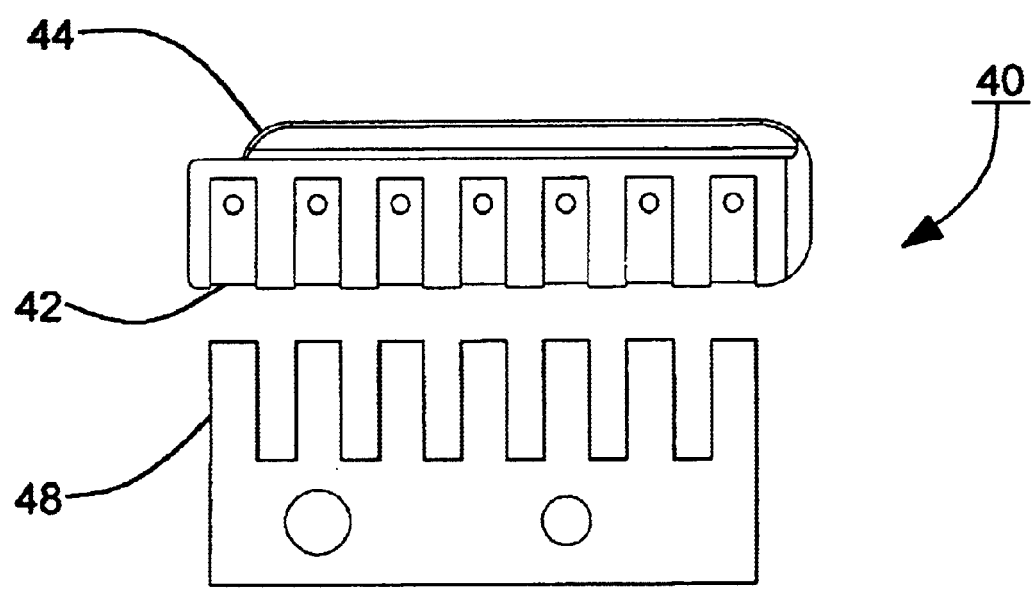

Turning now to FIG. 3, a six-pin feedthrough connector 40 is shown in accordance with one embodiment of the present invention. The connector 40 comprises six contacts 42 that are placed in contact with a molded plastic housing 44. A stamped insert 46 comprising the contacts 42 and a connecting tab 48 provide for the secure placement of the contacts 42 in relation to the applied plastic housing 44. The tab 48 can be removed from the connector 40 by breaking at a scribe mark 50 or by other means, for example, cutting, tearing or burning.

Figures 4A, 4B:
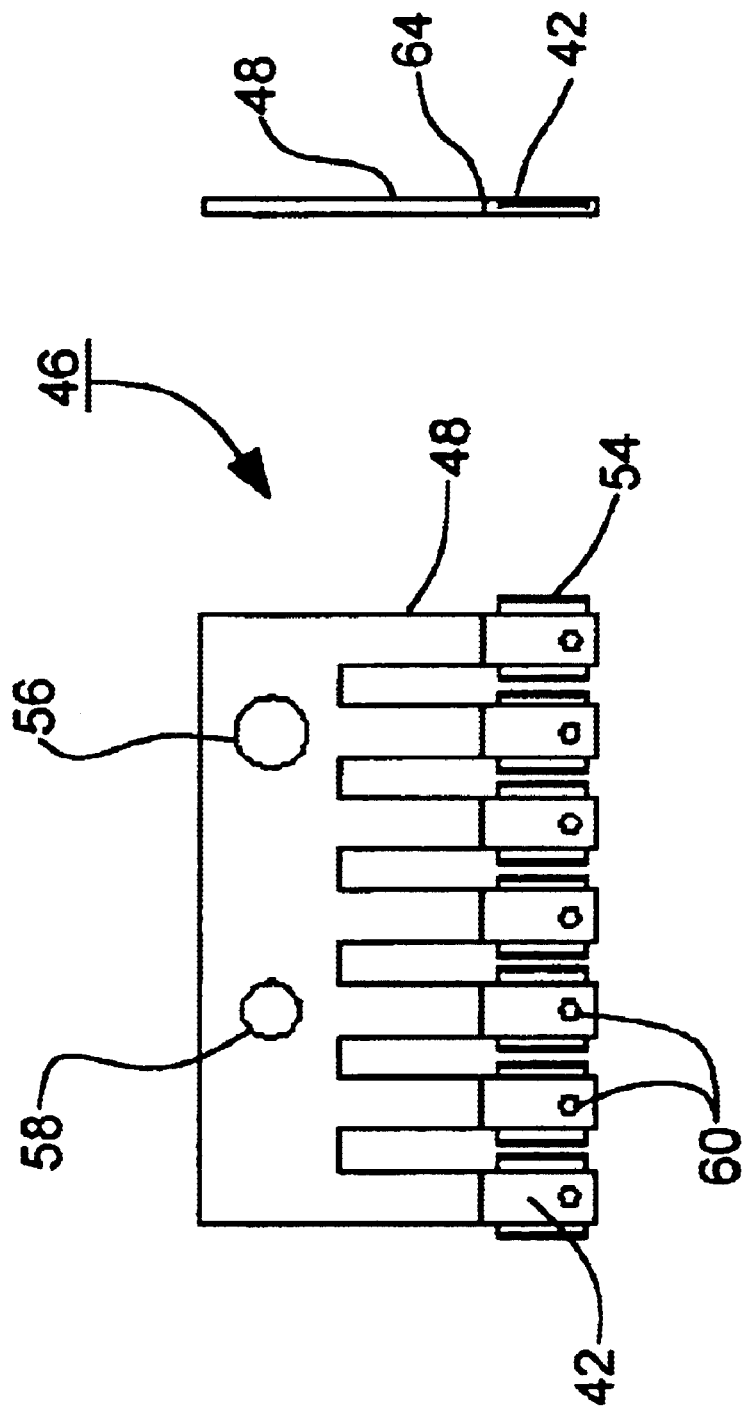
FIGS. 4A and 4B show a single stamped insert to be used to provide multiple contacts within an embodiment of the present invention.

FIGS. 4A and 4B present top and side views of an embodiment of the stamped insert 46. The embodiment shown in this embodiment has seven contacts 42 attached to the stamped insert 46. The contacts 42 comprise a tail extension 52 that protrudes from the contact 42 and is typically at a slight angle from the plane of the insert 46. Also protruding from the contact are side extensions 54. Recesses 56 between the tail extension 52 and the side extensions 54 enable at least a portion of the tail extension 52 and the side extensions 54 to be enclosed within the plastic housing as it is molded onto the insert 46 during the manufacturing process. The tail extension 52 and side extensions 54 provide stability and increased contact area between the insert 46 and the housing. A large alignment hole 56 and a small alignment hole 58 are shown which may provide correct alignment of the insert 46 during the manufacturing and molding process. The connection point 64 between the connecting tab 48 and the contacts 42 can comprise scribe marks on one or both sides of the insert 46.

Referring to FIGS. 5A–D, various perspective views of the contact 42 are shown after it has been disconnected from the connecting tab 48. Holes 60 in the contacts 42 provide a means of connecting the contact 42 with an electrical wire. A bevel 62 may be incorporated with the holes 60 to facilitate the guiding of the electrical wire through the hole 60. The top surface 66 of the contact 42 provides a surface for electrical contacts to be made, typically by means of welding of an electrical wire to the surface 66.

Figure 6:
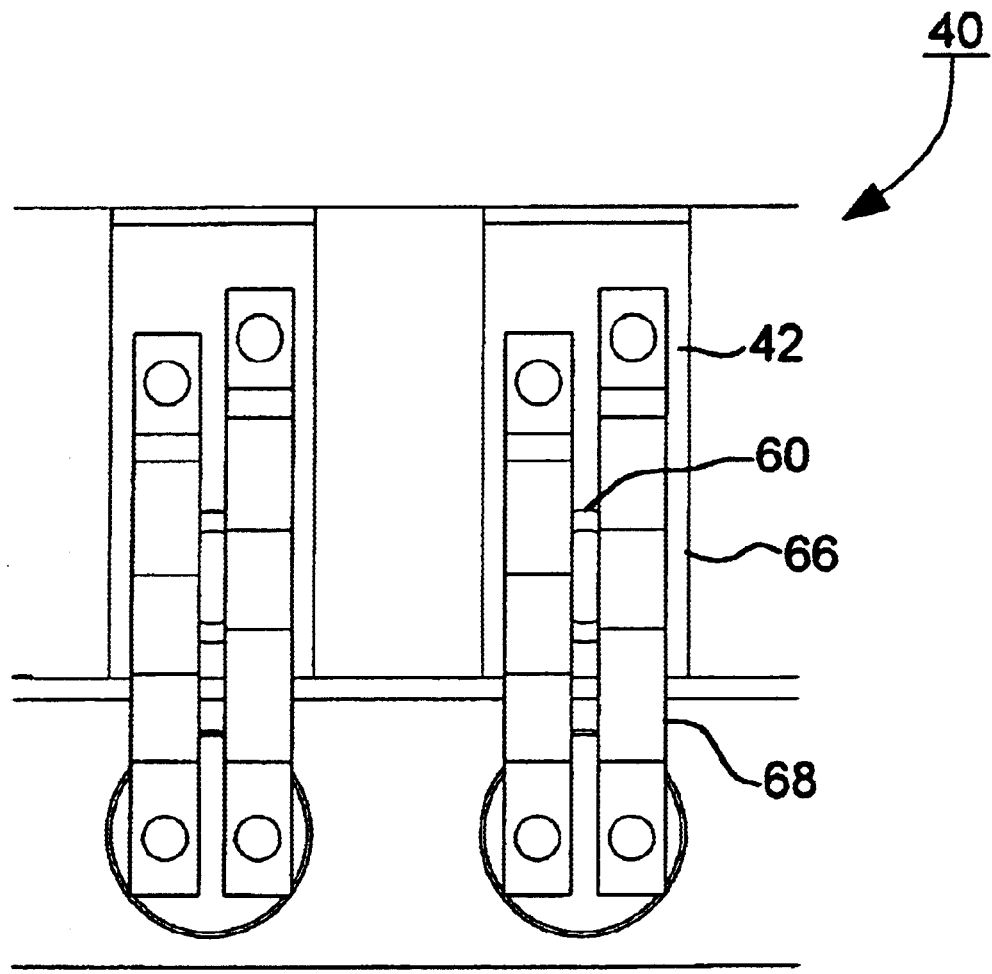
FIG. 6 is a photograph of one embodiment of the present invention comprising a molded connector 40 in use within a neural stimulator.

FIG. 6 is a photograph of one embodiment of the present invention comprising a six-pin strip molded connector 40 in use within a neural stimulator. Electrical wires 68 are in connection with the surface 66 of the individual contacts 42. In one embodiment, the holes 60 within the contacts 42 have been filled by the welding of wires that proceed from under the contacts 42, through the holes 60 and are welded in place to the contacts 42.

Figure 7:
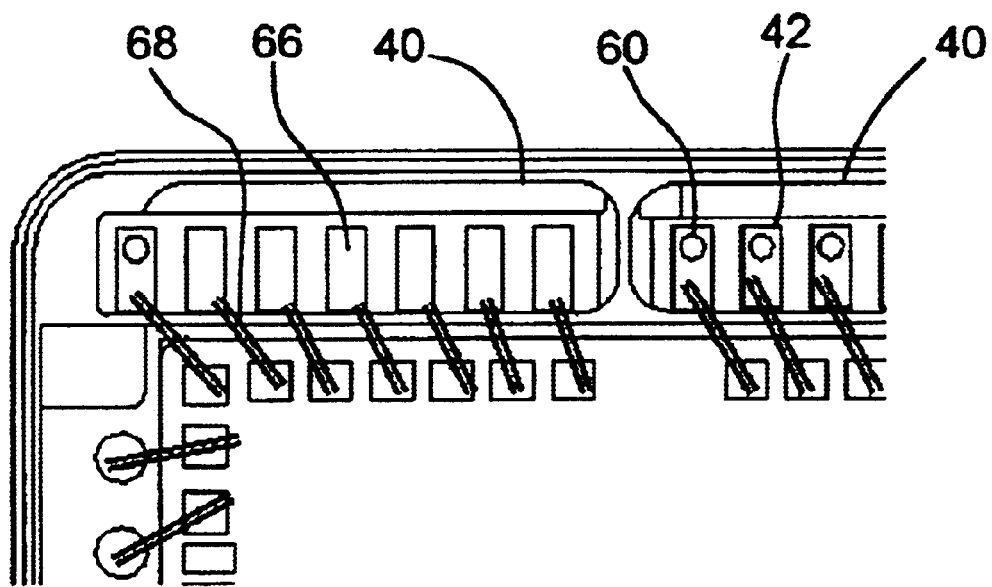
FIG. 7 is a photograph of an application of multiple embodiments of the present invention in use within a neural stimulator.

FIG. 7 is a photograph of an application of embodiments of the present invention comprising a plurality of six-pin strip molded connectors 40 in use within a neural stimulator. Three sets of the six-pin strip molded connectors 40 are shown connected to other components. Pairs of electrical wires 68 are connecting other electrical components with the surface 66 of the individual contacts 42. Connecting the components to the contacts 42 using pairs of electrical wires 68 provides redundancy in case the connection of a single wire were to fail. The holes 60 within the contacts 42 have been filled by the welding of wires that proceed from under the contacts 42, through the holes 60 and are welded in place to the contacts 42.

Figure 8A:
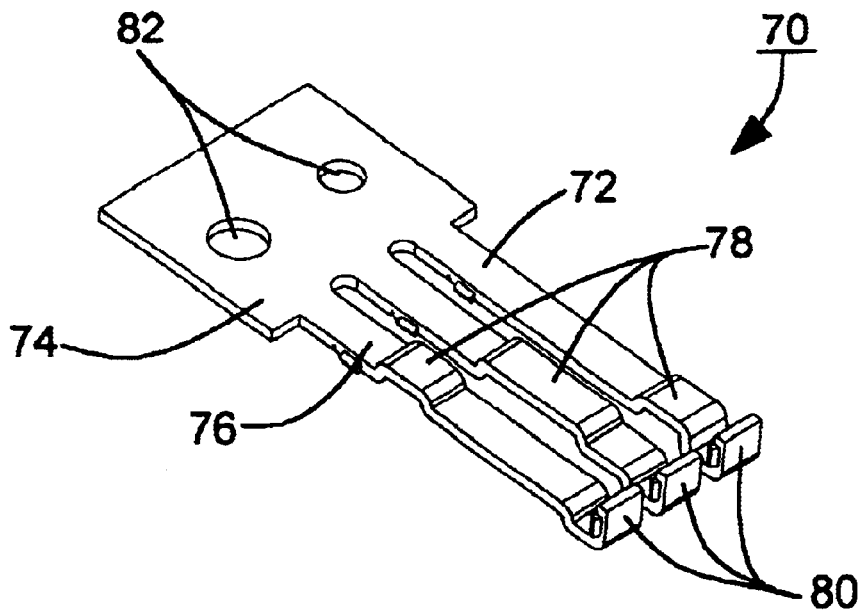
FIGS. 8A–B present profile views of the top and bottom of an embodiment of a stamped insert 70.
Figure 8B:
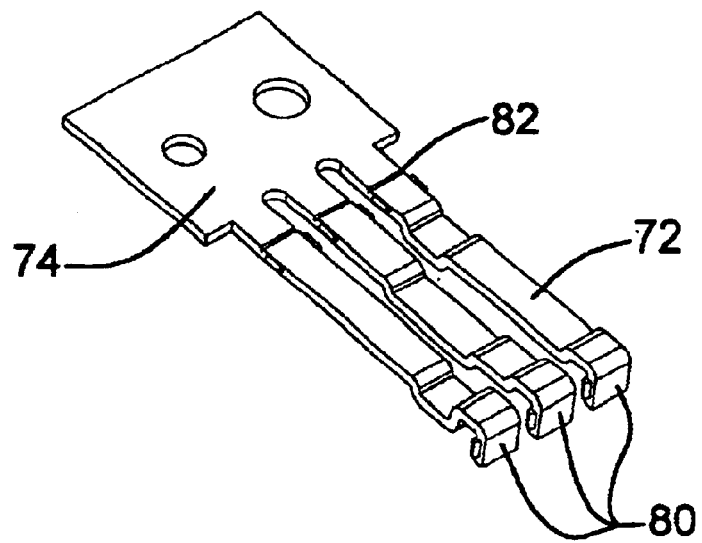

FIGS. 8A and 8B present profile views of the top and bottom of an embodiment of a stamped insert 70. In this particular embodiment the stamped insert 70 comprises three contact strips 72 that are connected to a tab 74. The contact strips 72 each comprise a first contact surface 76 that is adjacent to the tab 74, a second contact surface 78 that is a raised section of the contact strip 72, and a third contact surface 80 that is on the end of the contact strip 72. A scribed notch 82 is on the bottom of the contact strip 72 that can facilitate the removal of the tab 74 once the housing has been applied. Holes 82 within the tab 74 are used to ensure proper alignment of the insert 70 during the application of the housing.

Figure 9A:
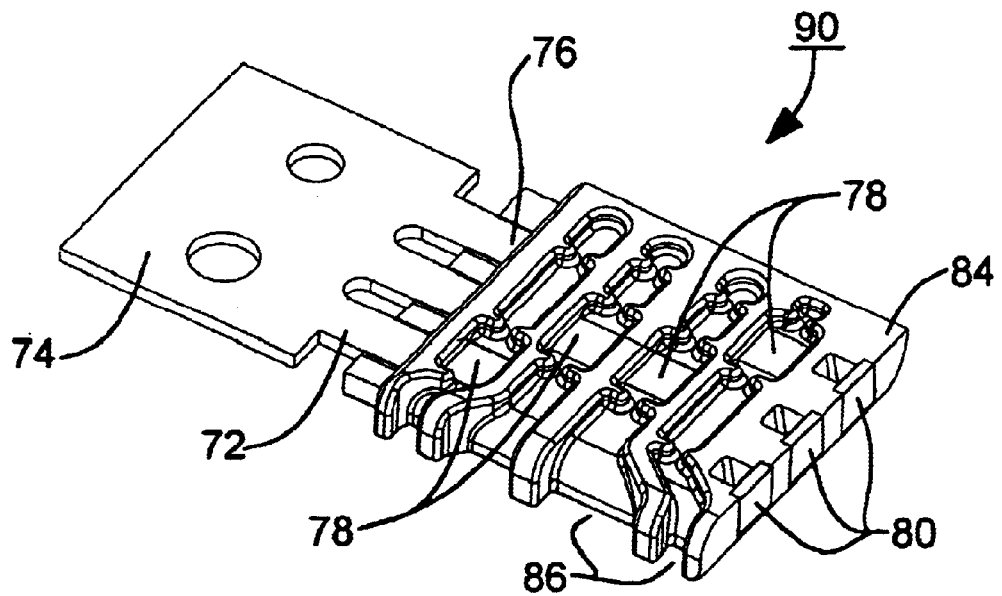
FIGS. 9A and 9B are profile views of a particular embodiment of the invention prior to removal of the insert tab.
Figure 9B:
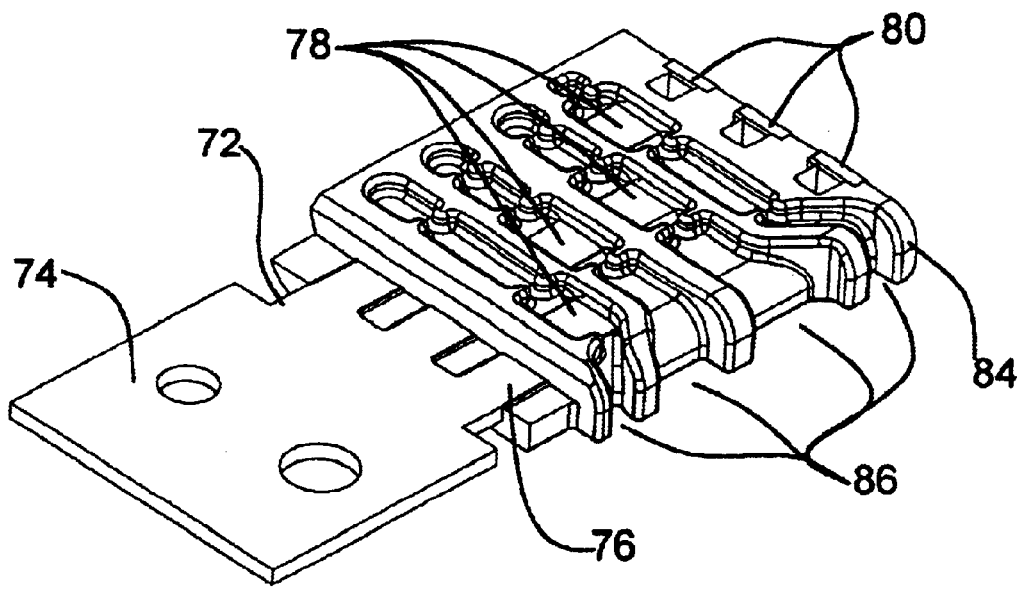

FIGS. 9A and 9B are profile views of a particular embodiment of the invention. A molded connector 90 is shown having a plastic housing 84 molded around the contact strips 72 shown in FIGS. 8A–B. The first, second, and third contact surfaces 76, 78, 80 on the contact strips 72 are exposed for future connection with electrical components. The molded housing 84 can comprise channels 86 that are capable of directing and separating the electrical wires. The channels 86 can separate wires that are to be connected to the individual contact surfaces 76, 78, 80 and reduce the risk of improper contacts between the wires. In this illustration the tab 74 is still connected to the contact strips 72.

Figure 10:
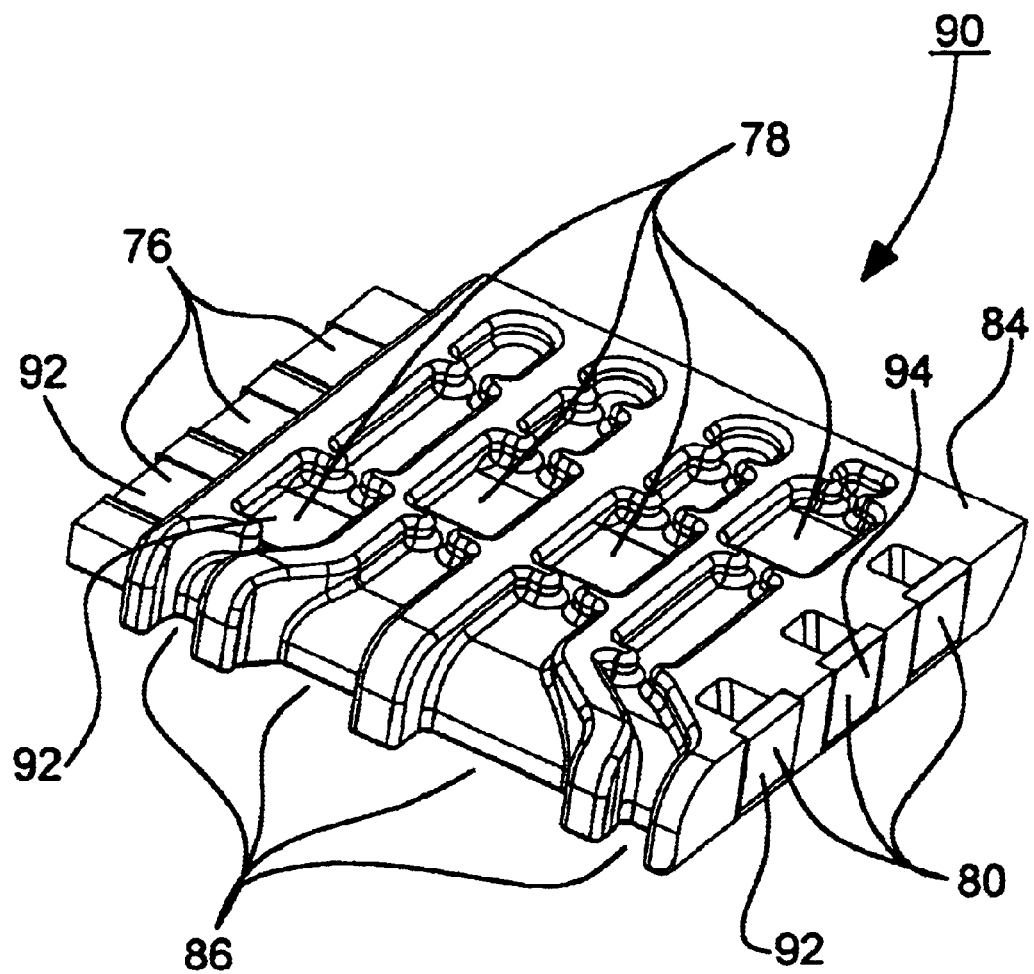
FIG. 10 is a profile view of a particular embodiment of the invention after removal of the insert tab.

Referring to FIG. 10, a molded connector 90 is shown after removal of the tab 74 shown in FIG. 9A from the molded connector 90. A first contact strip 92 is shown having a first contact surface 76, a second contact surface 78 and a third contact surface 80. An electrical connection to any of the three contact surfaces of the first contact strip 92 will be in electrical contact with the other two contact surfaces of the first contact strip 92. The middle contact strip 94 has a first contact surface 76, two second contact surfaces 78 and one third contact surface 80.

Figure 11:
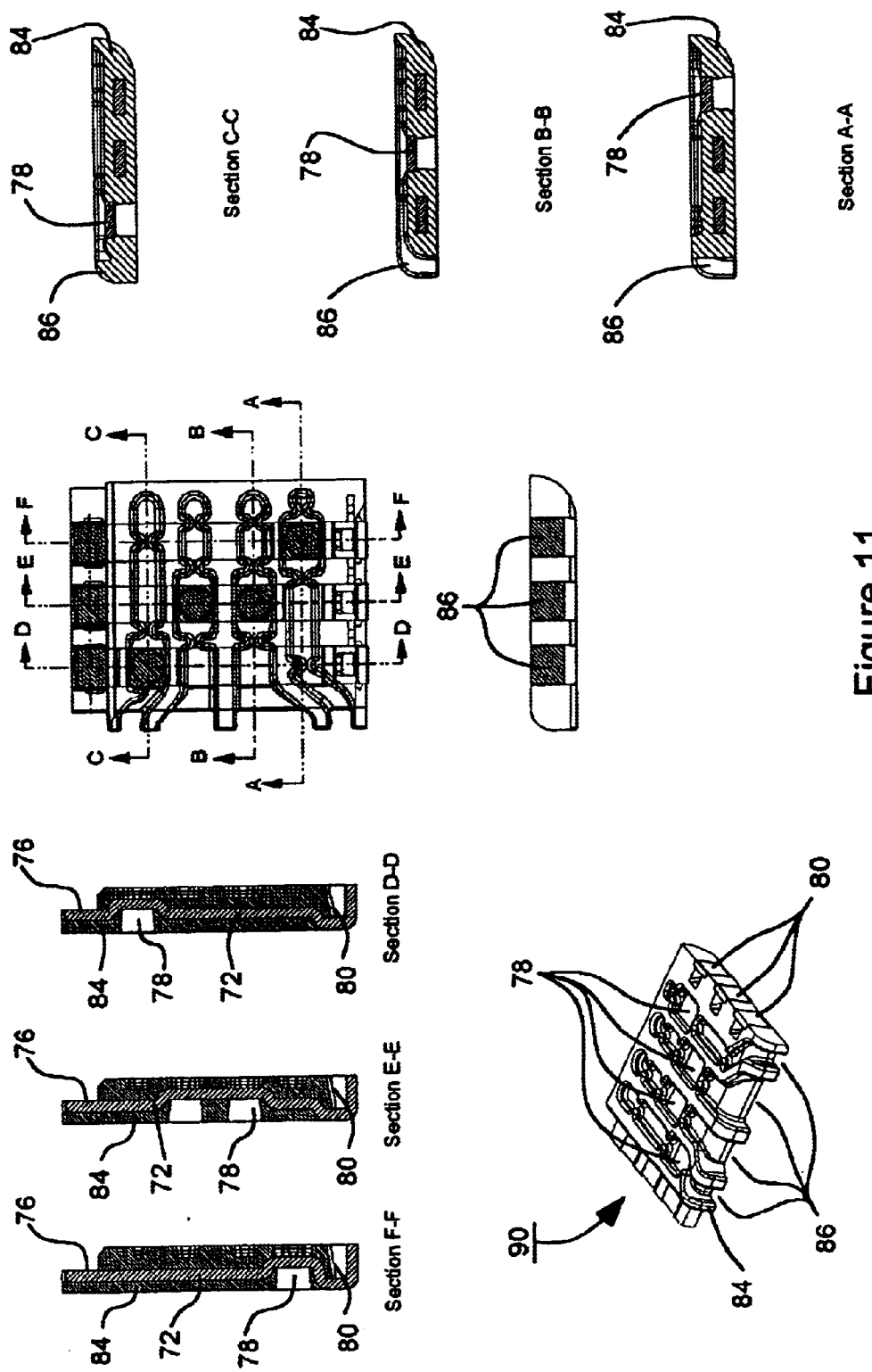
FIG. 11 illustrates various cross-sectional views of the embodiment shown in FIG. 10.

FIG. 11 illustrates various cross-sectional views of a molded connector 90 comprising a molded housing 84 enclosing a plurality of electrical contact strips 72. The housing 84 encloses a portion of the contact strips 72 and electrically insulates them. Exposed areas of the contact strips 72 provide a first contact surface 76, a second or middle contact surface 78 and a third contact surface 80 for each contact strip 72. Channels 86 within the housing 84 provide pathways for electrical components, such as wires, to be connected to the middle contact surfaces 78, while physically separated from the other contact surfaces, such as the third contact surfaces 80.

Figure 12:
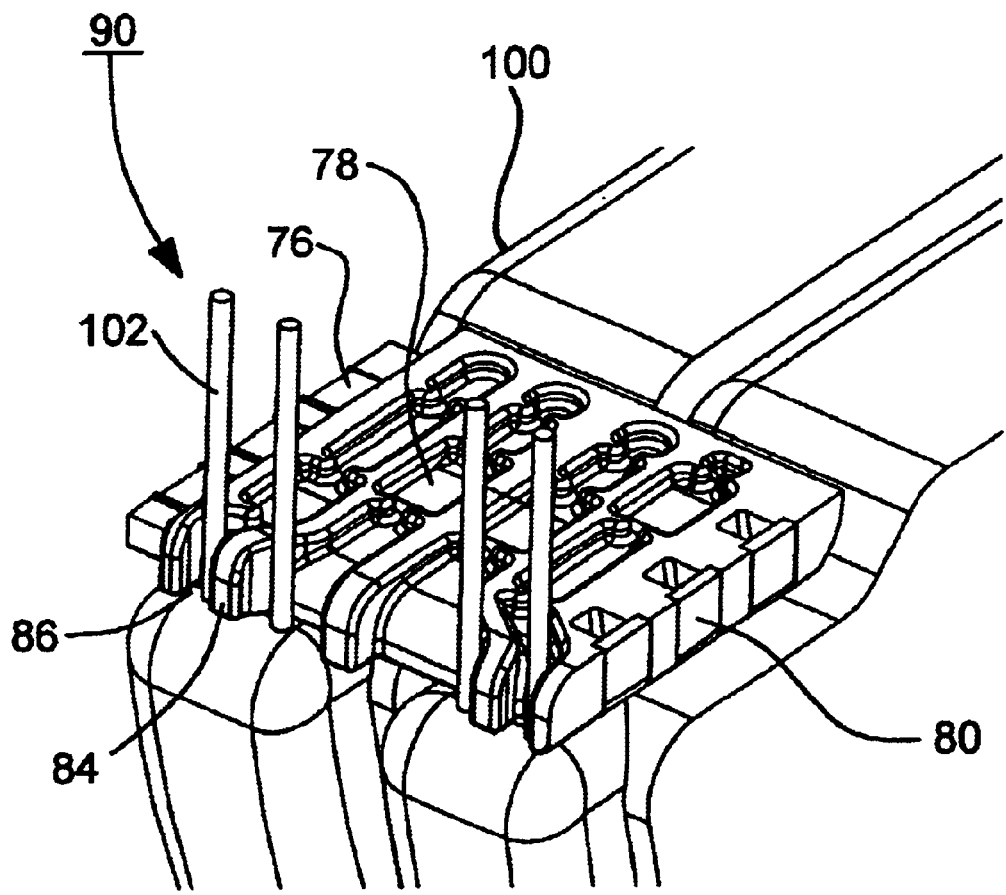
FIG. 12 shows the placement of the embodiment shown in FIG. 10 positioned adjacent to an electrical component.

FIG. 12 shows the placement of the molded connector 90 positioned adjacent to an electrical component 100. The electrical component 100 comprises a number of electrical wires 102, the electrical wires 102 are located within the channels 86 of the molded connector 90, the electrical wires 102 at least partially separated by the housing 84 of the molded connector 90. The electrical wires 102 can be bent and positioned to a location where each of them can be welded to one of the second contact surfaces 78. The first and third contact surfaces 76, 80 are available for contact with other electrical wires and other components. The combination of the electrical component 100 and the molded connector 90 can be utilized as a single piece when assembling a multi-component electrical device, such as in an implantable medical device.

Figure 13A:
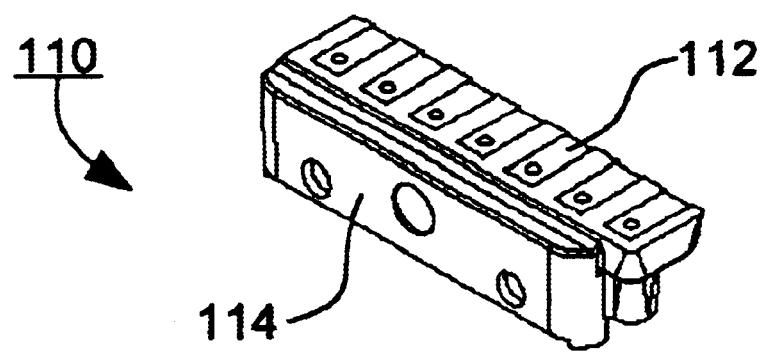
FIG. 13 shows multiple perspective views and cross-sectional illustrations of another alternate embodiment of the invention comprising an electrical connector.
Figure 13B:
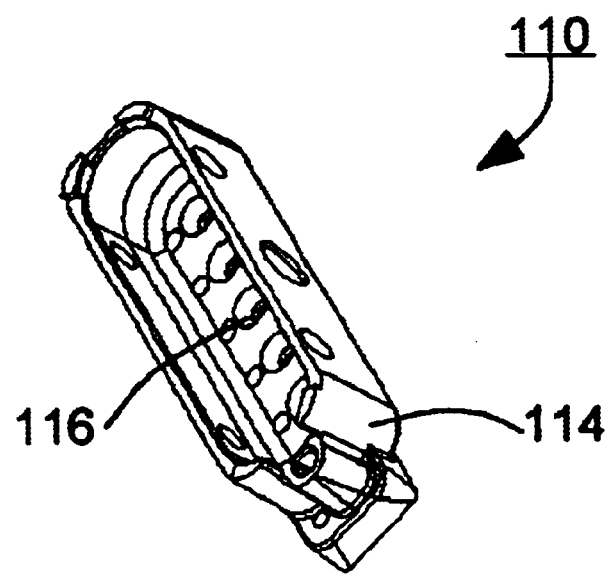

FIG. 13 show multiple perspective views and cross-sectional illustrations of another alternate embodiment of the invention comprising an electrical connector 110. In this particular embodiment, six contacts 112, similar to the ones shown in FIGS. 3 and 4, are positioned within a molded frame housing 114. The housing 114 comprises feedthrough holes 116 in which electrical wires can be disposed for connection with the contacts 112.

Figure 14:
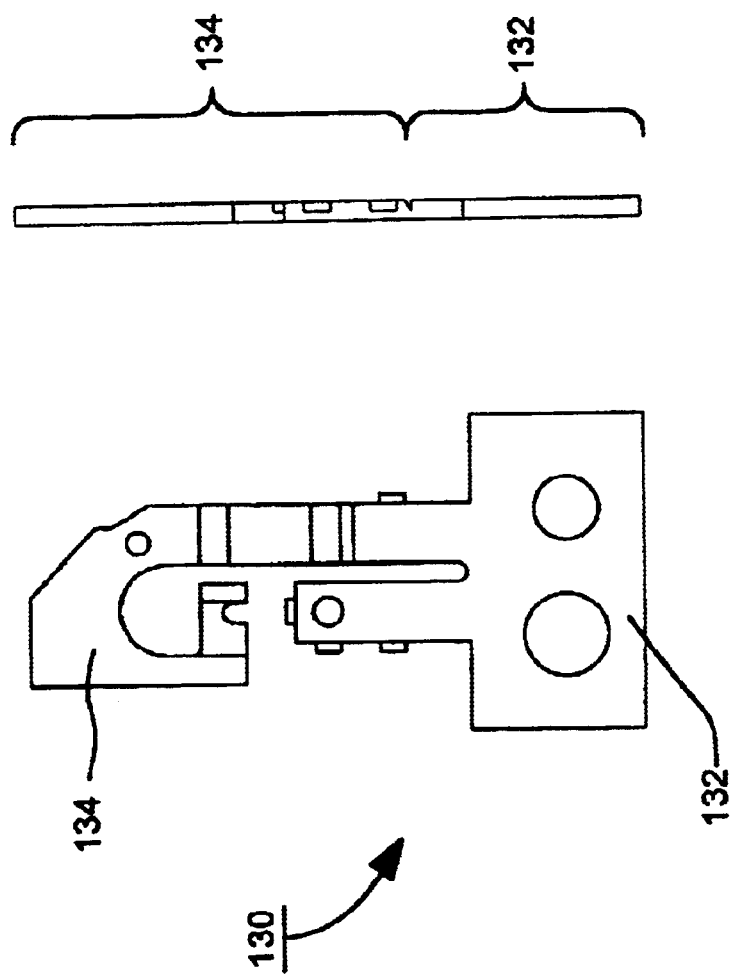
FIG. 14 shows a front and side view of a stamped insert prior to forming used within an embodiment of the present invention.
Figure 16:
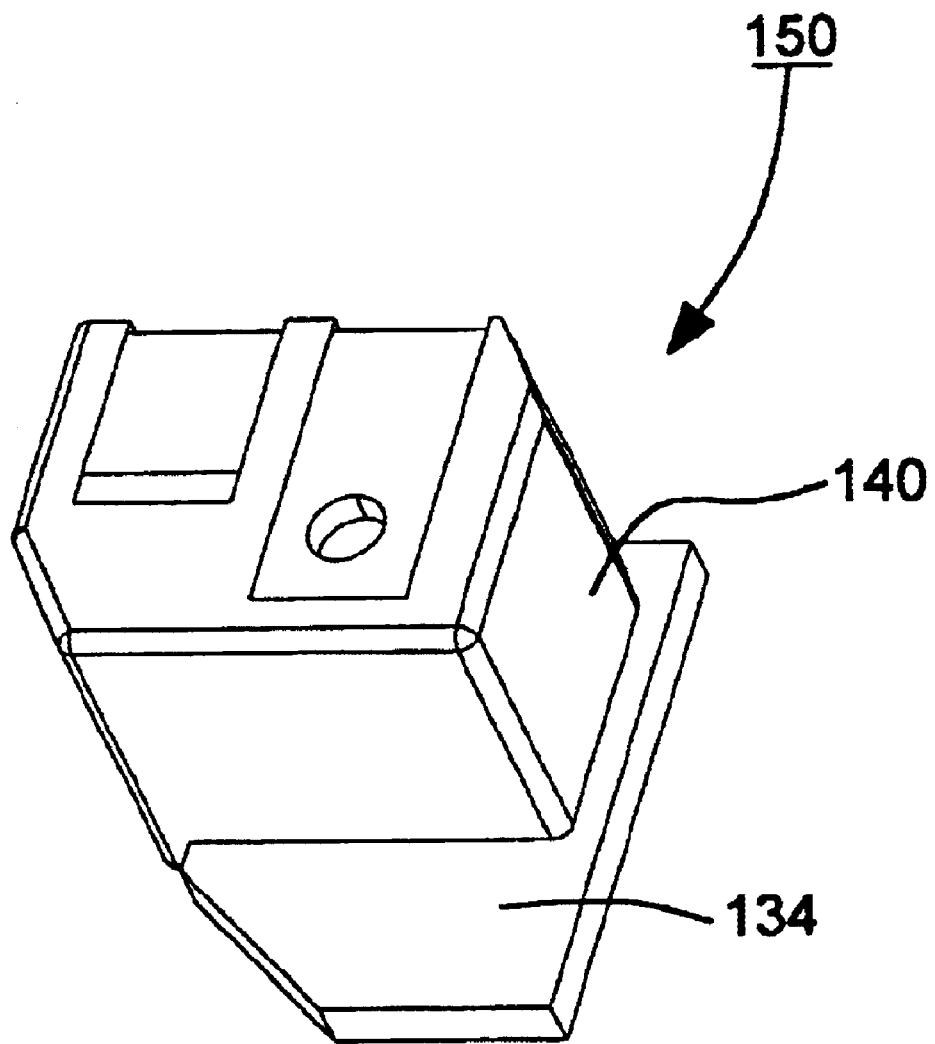
FIGS. 16A–F show multiple schematic views of an embodiment of the present invention.

FIGS. 14–16 illustrate an alternate embodiment of the invention. FIG. 14 shows a front and side views of a stamped insert 130 having a detachable tab section 132 and a contact section 134. Scribe marks 136 facilitate the breaking of the tab section 132 from the contact section 134. The stamped insert 130 is flat in its initial configuration.

FIGS. 15A–15F show multiple perspective views in which the stamped insert 130 is bent and reconfigured into the shaped insert 130 shown in FIG. 15F. The contact section 134 of the insert 130 then has a housing molded around it. The tab section 132 of the insert 130 is left outside of the housing that is molded around the contact section 134, enabling the tab section 132 to be disconnected from the contact section 134. The insert 130 typically comprises a scribe mark 136 that facilitates the removal of the tab section 134 from the contact section 134 once the molded housing has been applied.

FIGS. 16A–16F show multiple views of the housing 140 molded to the contact section 134 after its removal from the tab section 132, resulting in the electrical connector 150 shown in FIG. 16F. For example, FIG. 16F shows a three-dimensional illustration of an electrical connector 150 comprising a molded housing 140 that encloses at least a portion of the contact section 134.

According to an illustrated embodiment of the present invention, the connector assembly can be constructed of a single base metal or a layering of materials, which may be gold or nickel plating in particular embodiments. It will be appreciated, however, that the connector assembly may be constructed of various other types of metals or other materials without departing from the scope of the present invention. For example, the connector assembly may be constructed from titanium or a titanium alloy.

In some illustrated embodiments the individual connectors comprise a rectangular shape. It will be appreciated that the connector need not necessarily be limited to the shape of a rectangle, but may take the form of other suitable shapes for making electrical contacts.

According to an illustrated embodiment of the present invention, the connector assembly is used within the system control portion of an implantable medical device. It will be appreciated that the connector assemblies disclosed in the present invention is not limited to use within the system control but may be used in other system components as well, for example within leads or connection blocks where the leads attach to the implantable device.

In some illustrated embodiments the housing is comprised of a molded plastic material. It will be appreciated however, that the housing material need not be plastic and can comprise any material that is non-conductive to electrical transmission, for example, glass or ceramic. The term "molded" within this application is meant to include alternate methods of application of the housing upon the electrical contacts, such as, for example, painting or immersion methods.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An electrical connector in combination with an implantable medical device (IMD), for establishing permanent electrical communication between internal components of the IMD wherein said internal components couple to deployable medical electrical leads, comprising:
    a molded housing of insulating material adapted to sealingly couple to a surface of the IMD, said housing comprising a plurality of contact pad-receiving interlocking structures;
    a metallic insert having each of a plurality of wire contact pads sealingly secured to one of the plurality of contact pad-receiving interlocking structures of the molded housing wherein said insert includes a manually removable tab attached to the plurality of wire contact pads of the stamped insert so the removable tab and wire contact pads are in common electrical communication, and wherein the wire contact pads are sized to receive an end portion of an electrical wire; and
    means formed in said molded housing adapted for guiding the end portion of the electrical wire to each wire contact pad.

2. A connector of claim 1, wherein the insulating material comprises moldable plastic and wherein the means formed in said molded housing further comprises at least one aperture.

3. A connector of claim 1, wherein the insulating material comprises one of the group: a glass material, a resin-based material, a thermoplastic material.

4. A connector of claim 1, wherein the metallic insert comprises a set of thin, spaced apart members.

5. The connector of claim 1, wherein the manually removable tab comprises a scribed line disposed on a surface of the manually removable tab.

6. An apparatus in combination with an implantable medical device (IMD), for permanently connecting electrically-conducting components of the IMD so that deployable medical electrical leads can be coupled thereto, comprising:
    at least one electrical connector comprising a tab section and a plurality of spaced-apart electrically conducting wire bonding pads in common electrical communication; and
    a non-conductive housing at least partially enclosing the plurality of spaced-apart electrically conducting wire bonding pads of the at least one electrical connector, wherein said non-conductive housing comprises a plurality of structures adapted to mechanically interlock and individually retain each of the spaced-apart electrically conducting wire bonding pads, and wherein the at least one electrical connector is adapted to assist manual separation of the tab section from the plurality of spaced-apart electrically bonding pads, and wherein the wire bonding pads comprise a substantially flat wire-receiving portion.

7. An apparatus according to claim 6, wherein the apparatus is adapted to provide electrical connection between a plurality of electrical components internal and external to the implantable medical device.

8. An apparatus according to claim 6, wherein the at least one electrical connector comprises a series of electrical connectors temporarily attached by the tab section and thereby temporarily commonly electrically coupled together.

9. An apparatus according to claim 8, wherein the series of electrical connectors are adapted to be manually segmented into discrete components.

10. An apparatus according to claim 6, wherein the apparatus is a component of a header assembly for an IMD.

11. An apparatus according to claim 6, wherein the housing further comprises one of an wire-admitting aperture and a wire-guiding groove feature adjacent one of the wire bonding pads.

12. An apparatus according to claim 6, wherein the housing comprises moldable plastic.

13. An apparatus according to claim 6, wherein the housing comprises one of the group: a glass material, a resin-based material, a thermoplastic material.

14. An apparatus according to claim 6, wherein the at least one electrical connector conducts electrical signals between a plurality of contact surfaces on each electrical connector, wherein the housing provides isolation between the at least one electrical connector and the spaced-apart electrically conducting wire bonding pads.

15. An apparatus according to claim 14, wherein a plurality of electrical wires which couple to a similar plurality of electrical components are welded to the plurality of electrical contacts.

16. An apparatus according to claim 6, wherein the at least one electrical connector comprise an electrically conductive metallic material.

17. An apparatus according to claim 6, wherein the at least one electrical connector comprise a base metal.

18. An apparatus according to claim 17, wherein the metal comprises one of the group: a gold material, a nickel material, and alloys thereof.

19. An apparatus according to claim 6, wherein the implantable medical device comprises at least one of a pacemaker, a cardioverter, a defibrillator, a neural stimulator, and a drug administering device.

20. A feedthrough arrangement in combination with an implantable medical device (IMD), for establishing permanent electrical communication between internal circuits of the IMD and at least one removeable remote electrical component, comprising:
   a plurality of spaced-apart electrical contacts for conducting electrical signals communicated through a plurality of elongated conductors in common electrical communication with a removable tab portion;
   a molded housing comprising an electrical insulating material, the molded housing enclosing a portion of the plurality of electrical contacts, the housing disposed in sealing engagement with said portion of the plurality of electrical contacts, the housing further comprising a plurality of apertures, wherein the plurality of apertures are adapted for receiving wire-bonded electrical wires for permanent connection with the plurality of electrical contacts; and
   wherein the feedthrough arrangement is a component of the IMD.

21. A feedthrough arrangement according to claim 20, wherein the housing comprises one of: a moldable plastic material, a thermoplastic material, a resin-based material.

22. A feedthrough arrangement according to claim 20, wherein the housing comprises one of: a glass material, a ceramic material, a dielectric material.

23. A feedthrough arrangement according to claim 20, further comprising:
   the housing having an opening and the housing defining a first side of the housing; and
   wherein the plurality of electrical contacts extend from the first side of the housing to a second side of the housing.

24. A feedthrough arrangement according to claim 20, wherein the plurality of apertures extend from a first side of the housing to a second side of the housing.

25. A feedthrough arrangement according to claim 23, wherein the plurality of electrical contacts conduct electrical signals between the first side and the second side and the housing provides isolation between the first and second sides.

26. A feedthrough arrangement according to claim 25, wherein the plurality of electrical contacts are welded to the electrical wires that are disposed through the plurality of apertures.

27. A feedthrough arrangement according to claim 20, wherein the plurality of electrical contacts comprise a metal.

28. A feedthrough arrangement according to claim 20, wherein the plurality of electrical contacts comprise a geometrically shaped member.

29. A feedthrough arrangement according to claim 28, wherein the plurality of electrical contacts comprise a base metal and wherein said base metal is chosen from the group comprising: a gold material, a nickel material, and alloys of the gold material and the nickel material.

30. A feedthrough arrangement according to claim 20, wherein the housing and the plurality of electrical contacts are disposed within a header module of an IMD.

31. A feedthrough arrangement according to claim 30, wherein the IMD comprises at least one of: a pacemaker, a cardioverter, a defibrillator, a neural stimulator, and a drug administering device.

32. An electrical connector in combination with an implantable medical device (IMD), for permanently coupling a plurality of elongated electrical wires to circuitry disposed within the IMD comprising:
   an insert member comprising a plurality of electrical contact pads and a connecting tab severably connected to the plurality of electrical contact pads; and
   an electrically insulative housing, the housing comprising discrete interlocking structures in contact with and retaining each of the plurality of electrical contact pads;
   wherein each of the contact pads of the electrical connector is a component in the IMD.

33. An electrical connector according to claim 32, wherein the connecting tab is readily manually detachable from the plurality of electrical contacts.

34. An electrical connector according to claim 32, wherein the plurality of electrical contact pads provide electrical communication between components operatively coupled to the IMD.

35. An electrical connector according to claim 32, wherein the electrically insulative housing comprises a moldable plastic material.

36. An electrical connector according to claim 32, wherein the electrically insulative housing comprises one of a glass material and a ceramic material.

37. An electrical connector according to claim 32, wherein the electrically insulative housing comprises a plurality of apertures capable of communicating electrical wires through the plurality of apertures and to the plurality of electrical contacts.

* * * * *